(12) United States Patent
Matsukawa et al.

(10) Patent No.: US 9,212,158 B2
(45) Date of Patent: Dec. 15, 2015

(54) METHOD FOR PREPARING A FATTY ACID DERIVATIVE

(75) Inventors: Tatsuya Matsukawa, Tokyo-to (JP); Noriyuki Yamamoto, Tokyo-to (JP)

(73) Assignee: R-TECH UENO, LTD., Tokyo (JP)

( * ) Notice: Subject to any disclaimer, the term of this patent is extended or adjusted under 35 U.S.C. 154(b) by 314 days.

(21) Appl. No.: 13/537,980

(22) Filed: Jun. 29, 2012

(65) Prior Publication Data
US 2013/0005996 A1 Jan. 3, 2013

Related U.S. Application Data

(60) Provisional application No. 61/503,753, filed on Jul. 1, 2011.

(51) Int. Cl.
*C07D 317/30* (2006.01)
*C07C 405/00* (2006.01)
*C07F 7/18* (2006.01)

(52) U.S. Cl.
CPC ............ *C07D 317/30* (2013.01); *C07C 405/00* (2013.01); *C07F 7/1856* (2013.01); *C07C 2101/08* (2013.01)

(58) Field of Classification Search
None
See application file for complete search history.

(56) References Cited

U.S. PATENT DOCUMENTS

| 7,321,057 | B2 * | 1/2008 | Hirata et al. | 562/503 |
|---|---|---|---|---|
| 2006/0036108 | A1 | 2/2006 | Hirata et al. | |
| 2007/0232838 | A1 * | 10/2007 | Iwabuchi et al. | 568/700 |
| 2009/0124806 | A1 * | 5/2009 | Iwabuchi et al. | 546/72 |
| 2013/0172543 | A1 * | 7/2013 | Iwabuchi et al. | 536/27.6 |

FOREIGN PATENT DOCUMENTS

| EP | 1 775 296 A1 | 4/2007 |
|---|---|---|
| JP | 2006-045231 A | 2/2006 |

OTHER PUBLICATIONS

Masatoshi Shibuya et al., "2-Azaadamantane N-Oxyl (AZADO) and 1-Me-AZADO: Highly Efficient Organocatalysts for Oxidation of Alcohols" Journal of the American Chemical Society, Jul. 5, 2006, pp. 8412-8413, vol. 128, No. 26.

J.B. Plumb et al., "Chemical Safety", C&EN, Jul. 16, 1990, p. 3.

* cited by examiner

*Primary Examiner* — Yate K Cutliff
(74) *Attorney, Agent, or Firm* — Sughrue Mion, PLLC

(57) ABSTRACT

A method for manufacturing a fatty acid derivative represented by formula (I) is provided:

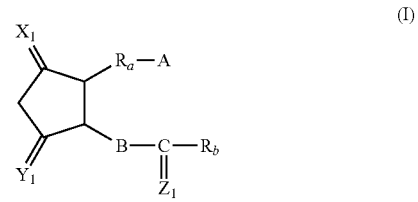

(I)

wherein $Z_1$ is

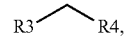

wherein R3 and R4 are hydrogen atom, halogen atom, lower alkyl or lower alkoxy; when R3 and R4 are lower alkoxy, R3 and R4 may be linked together to form a ring structure; which includes the step of reacting a compound of formula (II):

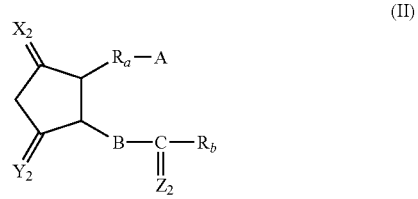

(II)

wherein $Z_2$ is the same as $Z_1$;
with a co-oxidizer under the presence of an azaadamantane-N-oxyl derivative.

6 Claims, No Drawings

METHOD FOR PREPARING A FATTY ACID DERIVATIVE

BACKGROUND OF THE INVENTION

Field of the Invention

The present invention relates to a novel method for manufacturing a fatty acid derivative that is useful as a medicament or a synthetic intermediate for a medicament.

Fatty acid derivatives are organic carboxylic acids existing in tissues and organs of human and the other mammals and have a wide variety of biological activity. Some fatty acid derivatives found in nature include those having, as a general structure thereof, a prostanoic acid skeleton as shown in the formula (A):

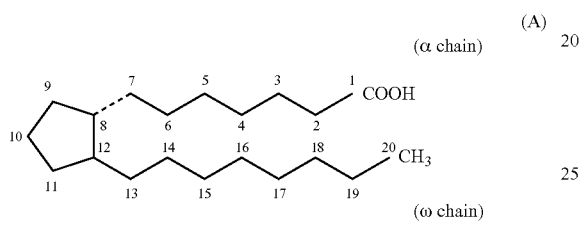

(A)

In preparing the fatty acid derivative such as prostaglandin derivatives having the above prostanoic acid skeleton, oxidation of a hydroxy group is one of important reaction steps. Many methods to oxidize a hydroxy group have been known.

Swern oxidation that has been conventionally used for prostaglandin syntheses requires special manufacturing equipment that can operate at a very low reaction temperature (−70 to −40° C.). In addition, when the fatty acid derivative has a carboxyl group in the molecular, undesired by-product could be a major product due to side reactions (See, for example, US2006-0036108A, especially, comparative example 1, this document is herein incorporated by reference). In order to avoid this problem, protection of the carboxyl group before Swern oxidation and de-protection of the protecting group after the oxidation are needed, as a result, the manufacturing process become long and redundant by these additional steps.

Furthermore, Swern oxidation co-generates dimethylsulfide that is strongly malodorous and therefore, equipment such as exhaust gas scrubber, activated carbon adsorption tower and the like are required for the malodor prevention.

Traditional oxidation method using heavy metal reagents such as chromic acid can be used for oxidation of compounds having carboxyl group. However, most of heavy metals are toxic and occasionally not suitable as an industrial production method for medicaments.

Dess-Martin oxidation also can be used to oxidize compounds having carboxyl group, however, the heat- and shock-sensitivity of this oxidizing reagent is reported (Chem. Eng. News, Jul. 16, 3, 1990, this document is herein incorporated by reference.). In addition, this oxidizing reagent is not easily available as an industrial raw material from the market. Accordingly, Dess-Martin oxidation is not suitable for industrial manufacture.

TEMPO oxidation is also used for the oxidation of hydroxy groups. This reaction can be easily carried out under relatively mild conditions and therefore, without using equipment such as ultralow temperature reactor and exhaust gas scrubber. It has been known as a method that can produce the product with high purity and high production efficiency (US 2006-0036108A, this document is herein incorporated by references). However, some problems of TEMPO oxidation have been known to the art. For example, the oxidized form of TEMPO, i.e. the active form of TEMPO, is structurally instable and therefore, the reaction needs a relatively large amount of the catalyst. In addition, when a bulky substrate is oxidized using TEMPO, enough reactivity can hardly be achieved. In order to promote the reaction, 1.0-2.0 molar equivalent of halide salt such as sodium bromide, potassium bromide, tetrabutylammonium bromide or tetrabutylammonium chloride per one molar equivalent of the hydroxy group is usually added to the reaction. Those halide salts may, however, cause the generation of by-products such as a bromide analogue.

Under the above discussed circumstances, an industrially applicable method for oxidizing a hydroxy group that can suppress the generation of by-product has been desired.

SUMMARY OF THE INVENTION

An object of the present invention is to provide a new method for manufacturing a fatty acid derivative, which can be easily carried out under relatively mild conditions.

The instant inventors have intensively studied and found that a fatty acid derivative can be effectively produced by oxidizing a synthetic intermediate using co-oxidizer in the presence of a azaadamantane-N-oxyl derivative. According to the method of the present invention, the desired fatty acid derivative can be synthesized by using an easy-available inexpensive co-oxidizer without special equipment, and generation of the undesired by-product is suppressed.

Accordingly, the present invention provides a method for manufacturing a fatty acid derivative represented by formula (I):

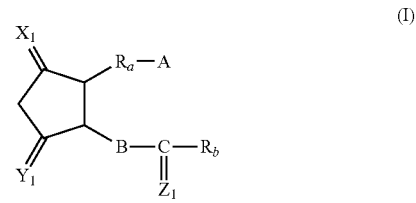

(I)

wherein $X_1$ is

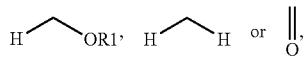

wherein R1 is a protecting group for hydroxy group; $Y_1$ is

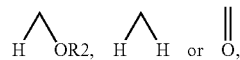

wherein R2 is a protecting group for hydroxy group; $Z_1$ is

wherein R3 and R4 are hydrogen atom, halogen atom, lower alkyl or lower alkoxy; when R3 and R4 are lower alkoxy, R3 and R4 may be linked together to form a ring structure; provided that at least one of $X_1$ and $Y_1$ is

A is —$CH_3$, —$CH_2OH$, —$COCH_2OH$, —COOH or a functional derivative thereof;

B is a single bond, —$CH_2$—, —$CH_2$—$CH_2$—, —CH=CH— or —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Ra is bivalent saturated or unsaturated lower-medium aliphatic hydrocarbon group, which is unsubstituted or substituted by halogen atom, lower alkyl, lower alkoxy, oxo, aryl or heterocyclic group, provided that one or more carbon atoms of the aliphatic hydrocarbon group may optionally be replaced with oxygen, nitrogen or sulfur atom; and Rb is hydrogen atom; saturated or unsaturated lower-medium aliphatic hydrocarbon group which is unsubstituted or substituted by a halogen, oxo, hydroxy, lower alkoxy, lower alkanoyloxy, cyclo(lower)alkyl, cyclo(lower)alkyloxy, aryl, aryloxy, heterocyclic or heterocyclic oxy; cyclo(lower)alkyl; cyclo(lower)alkyloxy; aryl; aryloxy; heterocyclic; or heterocyclic oxy, which comprises the step of, reacting a compound of formula (II):

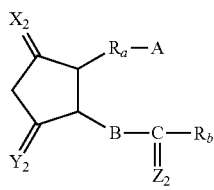

(II)

wherein, $X_2$ is the same as $X_1$ except for when $X_1$ is

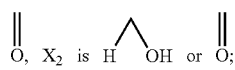

$Y_2$ is the same as $Y_1$ except for when $Y_1$ is

$Z_2$ is the same as $Z_1$, provided that at least one of $X_2$ and $Y_2$ is

and, A, B, Ra and Rb are the same as above;

with a co-oxidizer under the presence of an azaadamantane-N-oxyl derivative.

DETAILED DESCRIPTION OF THE INVENTION

In the definition of above Ra and Rb, the term "unsaturated" in the definitions for Ra and Rb is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower-medium aliphatic hydrocarbon" means a hydrocarbon having a straight or branched chain of 1 to 14 carbon atoms, wherein the side chain has preferably 1 to 3 carbon atoms. The preferred Ra has 1 to 10, more preferably, 6 to 10 carbon atoms, and the preferred Rb has 1 to 10, more preferably, 1 to 8 carbon atoms.

The term "halogen" includes fluorine, chlorine, bromine, and iodine atoms.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O— wherein the lower alkyl is as described above.

The term "lower alkanoyloxy" means a group represented by the formula RCO—O—, wherein RCO— is an acyl formed by oxidation of a lower alkyl as described above, for example, acetyl.

The term "lower cycloalkyl" means a group formed by cyclization of a lower alkyl group containing 3 or more carbon atoms as described above, for example, cyclopropyl, cyclobutyl, cyclopentyl, and cyclohexyl.

The term "cyclo(lower)alkyloxy" means a group represented by the formula cycloalkyl-O—, wherein cycloalkyl is described above.

The term "aryl" includes aromatic hydrocarbon rings (preferably monocyclic groups), which may be substituted, for example, phenyl, tolyl and xylyl. Examples of the substituents in this case include halogen, and halogen substituted lower alkyl group, wherein halogen atom and lower alkyl group are as described above.

The term "aryloxy" means a group represented by the formula ArO—, wherein Ar is an aryl group as described above.

The term "heterocyclic" includes mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur atoms. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy" means a group represented by the formula HcO—, wherein Hc is a heterocyclic group as described above.

The term "functional derivative" of A includes salts, preferably pharmaceutically acceptable salts, ethers, esters, and amides.

Examples of suitable "pharmaceutically acceptable salts" include nontoxic salts which are commonly used, and salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy (lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidophenyl ester; and aryl(lower)alkyl esters such as benzyl ester, trityl ester, and benzhydryl ester.

An amide for A is a group represented by formula: —CONR'R", wherein R' and R" independently represent hydrogen atom, lower alkyl, aryl, alkyl- or aryl-sulfonyl, lower alkenyl or lower alkynyl. Examples of amides include mono- or di-lower alkyl amides such as methylamide, ethylamide, and dimethylamide; aryl amides such as anilide, and toluidide; and alkyl- or aryl-sulfonyl amides such as methylsulfonyl amide, ethylsulfonyl amide, and tolylsulfonyl amide.

Preferred examples of A include —COOH, and a pharmaceutically acceptable salt, an ester and an amide thereof.

Preferred B is —CH$_2$—CH$_2$— which provides the structure of so-called, 13,14-dihydro type derivative.

Preferred Ra is a hydrocarbon having 1-10 carbon atoms, more preferably, 6-10 carbon atoms. One or more carbon atom of the hydrocarbon group may optionally be replaced with oxygen, nitrogen or sulfur atom.

Examples of Ra include, for example, the following groups:

—CH$_2$—CH$_2$—CH$_2$—CH$_2$—CH$_2$—CH$_2$—,
—CH$_2$—CH═CH—CH$_2$—CH$_2$—CH$_2$—,
—CH$_2$—CH$_2$—CH$_2$—CH$_2$—CH═CH—,
—CH$_2$—C≡C—CH$_2$—CH$_2$—CH$_2$—,
—CH$_2$—CH$_2$—CH$_2$—CH$_2$—CH(CH$_3$)—CH$_2$—,
—CH$_2$—CH$_2$—CH$_2$—CH$_2$—O—CH$_2$—,
—CH$_2$—CH═CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH═CH—CH$_2$—CH$_2$—CH$_2$—CH$_2$—,
—CH$_2$—CH$_2$—CH$_2$—CH$_2$—CH$_2$—CH═CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH═CH—CH$_2$—CH$_2$—CH$_2$—CH$_2$—CH$_2$—,
—CH$_2$—CH$_2$—CH$_2$—CH$_2$—CH$_2$—CH$_2$—CH═CH—,
—CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH(CH$_3$)—CH$_2$—,

Preferred Rb is a hydrogen atom or a hydrocarbon containing 1-10 carbon atoms, more preferably, 1-8 carbon atoms that is substituted by halogen atom such as fluorine.

In the specification and claims, the term "protecting group for hydroxy group" means a functional group which is introduced to protect the hydroxy group from oxidation. In the present invention, the protecting group may be any group as long as it can act as such. Examples of the protecting groups may include methyl, methoxymethyl, ethyl, 1-ethoxyethyl, benzyl, substituted benzyl, allyl, tetrapyranyl, t-butyldimethylsilyl, triethylsilyl, triisopropylsilyl, diphenylmethylsilyl, formyl, acetyl, substituted acetyl, benzoyl, substituted benzoyl, methyloxycarbonyl, benzyloxycarbonyl, t-buthloxycarbonyl and allyloxycarbonyl groups.

Examples of azaadamantane-N-oxyl derivatives that can be used in the present invention include, but are not limited to, 2-azaadamantane-N-oxyl (AZADO) and 1-methyl-2-azaadamantane-N-oxyl (1-Me-AZADO). The azaadamantane-N-oxyl derivative also includes chemical substances generating the same chemical species as an active oxidative species obtained from 2-azaadamantane-N-oxyl (AZADO), 1-methyl-2-azaadamantane-N-oxyl (1-Me-AZADO), or the like, by use of a co-oxidizer in a reaction system. Examples thereof include, but are not limited to, 2-hydroxy-2-azaadamantane (AZADOL [registered trademark of Nissan Chemical Industries, Ltd.]), 2-hydroxy-1-methyl-2-azaadamantane (1-Me-AZADOL), and the like.

The amount of the azaadamantane-N-oxyl derivative used in the reaction may be about 0.0005-1.0 mole, preferably about 0.001-0.1 mole per one mole of the starting compound to be oxidized or a compound of formula (II).

The co-oxidizer used in the present invention is one which can convert (i) the azaadamantane-N-oxyl derivative into an active oxidative species thereof; (ii) a reduced form of azaadamantane derivative (for example, 2-hydroxy-2-azaadamantane), which is generated upon oxidation of a substrate, again into the active oxidative species, as shown in the following scheme. Examples of co-oxidizers may include hypohalogenous acid such as hypochlorous acid or a salt thereof, halogenous acid such as bromous acid or a salt thereof, compounds having polyvalent iodine such as iodobenzene acetate, peroxides such as 3-chloro-perbenzoide acid, N-halogen substituted succinimides such as N-chloro succinimide.

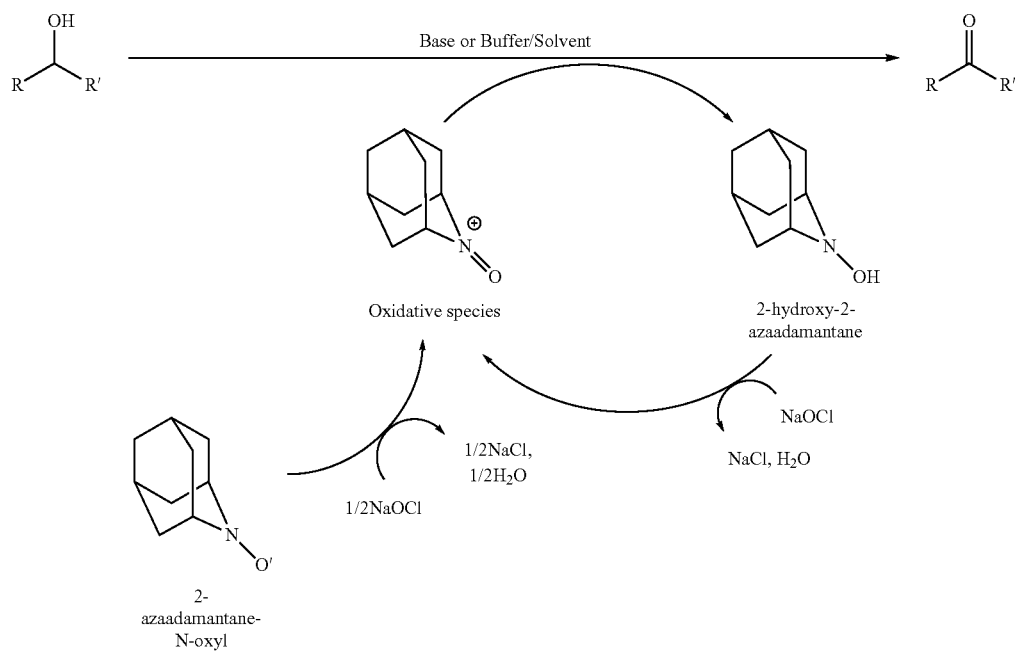

Catalytic Cycle and Action of Co-Oxidizer (for Example, Sodium Hypochlorite)

The amount of the co-oxidizer in the reaction may be 1.0-3 molar equivalents, preferably 1.1-2 molar equivalents and more preferably 1.1-1.5 molar equivalents per one molar equivalent of the hydroxy group to be oxidized.

The reaction may be conducted in an organic solvent, an aqueous solvent, a mixture thereof, or a two-phase solvent system consisting of an organic and an aqueous solvents.

Examples of organic solvents used in the present invention may be aromatic hydrocarbon solvent such as toluene, aliphatic hydrocarbon solvent such as hexane, halogen-containing solvent such as dichloromethane, ketones such as acetone, esters such as ethyl acetate.

The aqueous solvent may contain a pH adjusting agent such as sodium hydrogen carbonate, pH buffer such as potassium dihydrogen phosphate and sodium dihydrogen phosphate.

According to the present invention, a halide salt such as sodium bromide, potassium bromide, tetrabutylammonium bromide, and tetrabutylammonium chloride may be added to the reaction in order to facilitate the reaction.

The amount of the halide salt to be added is not limited and may be about 0.05-0.5 molar equivalents per one molar equivalent of the hydroxy group to be oxidized. In contrast, when TEMPO (tetramethylpiperidine-1-oxyl) is used instead of azaadamantane-N-oxyl derivative, 1.0-2.0 molar equivalents of TEMPO per one molar equivalent of the hydroxy group to be oxidized are required.

According to the present invention, the reaction may be carried out at a temperature of −10 to 50° C., preferably, about 0 to 20° C.

The present invention will be illustrated in more detail by way of the following examples. These examples should not be used as any limitation of the present invention.

Example 1

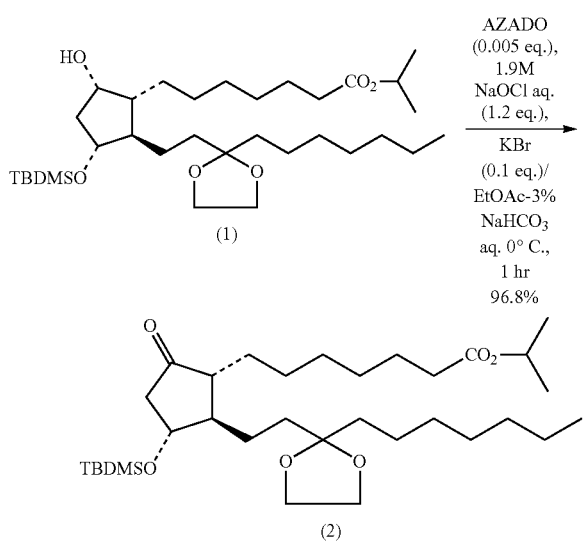

An alcohol compound (1) 0.200 g (0.34 mmol) was dissolved in ethyl acetate (1.4 ml), and then AZADO (1 mg/ml in ethyl acetate 0.3 ml, 0.0017 mmol) was added thereto. The mixture was cooled in an ice bath to 0° C. Three percent aqueous sodium hydrogen carbonate 1.91 ml (0.68 mmol)

and potassium bromide 4.1 mg (0.034 mmol) were added thereto. Then, 1.9M aqueous sodium hypochlorite 0.22 ml (0.41 mmol) was added dropwise to the reaction, and the mixture was stirred at 0° C. for 1 hour. The reaction mixture was then added with saturated aqueous sodium thiosulfate, and the mixture was extracted three times with ethyl acetate. The extract was washed with dilute hydrochloric acid, saturated aqueous sodium hydrogen carbonate and then, saturated saline, dried with anhydrous magnesium sulfate, filtered and concentrated under reduced pressure. The residue was purified with silica gel flash chromatography (column: BW-300SP 60 g, ethyl acetate:hexane=1:5) to give compound (2) as colorless oil. Yield 0.1929 g (96.8%)

$^{1}$H-NMR (400 MHz in CDCl$_3$, TMS=0 ppm) δ: 0.05 (3H, s), 0.08 (3H, s), 0.85-0.90 (12H, m), 1.23 (6H, d, J=6.3 Hz), 1.21-1.91 (28H, m), 2.15 (1H, dd, J=6.1, 18.0 Hz), 2.24 (2H, t, J=7.6 Hz), 2.56 (1H, m), 3.89-3.95 (4H, m), 4.03 (1H, m), 5.00 (1H, septet, J=6.3 Hz)

Example 2

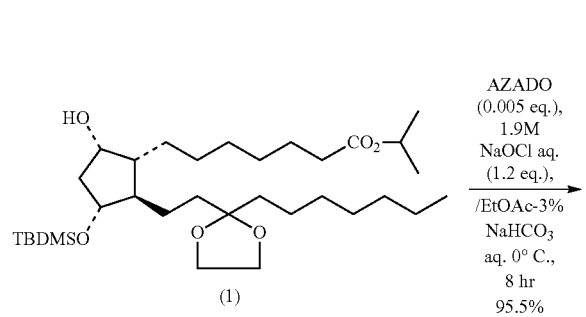

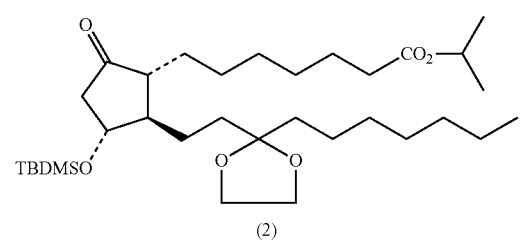

An alcohol compound (1) 0.200 g (0.34 mmol) was dissolved in ethyl acetate (1.4 ml), and then AZADO (1 mg/ml in ethyl acetate 0.3 ml, 0.0017 mmol) was added thereto. The mixture was cooled in an ice bath to 0° C. Three percent aqueous sodium hydrogen carbonate 1.91 ml (0.68 mmol) were added thereto. Then, about 1.9M aqueous sodium hypochlorite 0.22 ml (0.41 mmol) was added dropwise to the reaction, and the mixture was stirred at 0° C. for 8 hours. The reaction mixture was treated and purified in the similar manner as Example 1 to give compound (2) as colorless oil. Yield 0.1903 g (95.5%)

$^{1}$H-NMR (400 MHz in CDCl$_3$, TMS=0 ppm) δ: 0.05 (3H, s), 0.08 (3H, s), 0.85-0.90 (12H, m), 1.23 (6H, d, J=6.3 Hz), 1.28-1.91 (28H, m), 2.15 (1H, dd, J=6.1, 18.0 Hz), 2.24 (2H, t, J=7.7 Hz), 2.56 (1H, m), 3.89-3.97 (4H, m), 4.04 (1H, m), 5.00 (1H, septet, J=6.3 Hz)

Example 3

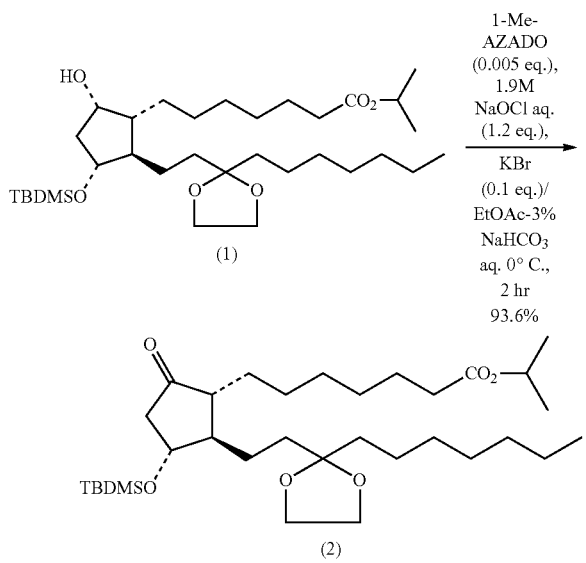

An alcohol compound (1) 0.200 g (0.34 mmol) was dissolved in ethyl acetate (1.4 ml), and then 1-Me-AZADO (1 mg/ml in ethyl acetate 0.3 ml, 0.0017 mmol) was added thereto. The mixture was cooled in an ice bath to 0° C. Three percent aqueous sodium hydrogen carbonate 1.91 ml (0.68 mmol) and potassium bromide 4.1 mg (0.034 mmol) were added thereto. Then, about 1.9M aqueous sodium hypochlorite 0.22 ml (0.41 mmol) was added dropwise to the reaction, and the mixture was stirred at 0° C. for 2 hours. The reaction mixture was treated and purified in the similar manner as Example 1 to give compound (2) as colorless oil. Yield 0.1866 g (93.6%)

$^{1}$H-NMR (400 MHz in CDCl$_3$, TMS=0 ppm) δ: 0.05 (3H, s), 0.08 (3H, s), 0.84-0.90 (12H, m), 1.23 (6H, d, J=6.3 Hz), 1.20-1.91 (28H, m), 2.15 (1H, dd, J=6.1, 18.0 Hz), 2.24 (2H, t, J=7.6 Hz), 2.56 (1H, m), 3.89-3.97 (4H, m), 4.04 (1H, m), 5.00 (1H, septet, J=6.3 Hz)

Example 4

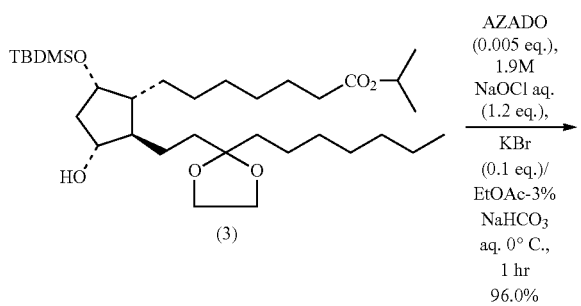

-continued

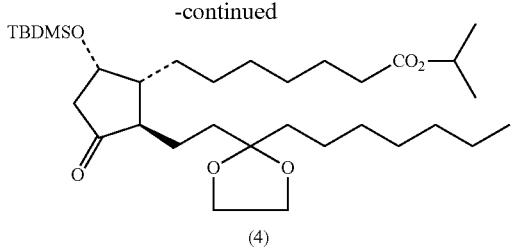

(4)

An alcohol compound (3) 0.200 g (0.34 mmol) was dissolved in ethyl acetate (1.4 ml), and then AZADO (1 mg/ml in ethyl acetate 0.3 ml, 0.0017 mmol) was added thereto. The mixture was cooled in an ice bath to 0° C. Three percent aqueous sodium hydrogen carbonate 1.91 ml (0.68 mmol) and potassium bromide 4.1 mg (0.034 mmol) were added thereto. Then, about 1.9M aqueous sodium hypochlorite 0.22 ml (0.41 mmol) was added dropwise to the reaction, and the mixture was stirred at 0° C. for 1 hour. The reaction mixture was treated and purified in the similar manner as Example 1 to give compound (4) as colorless oil. Yield 0.1914 g (96.0%)

$^1$H-NMR (400 MHz in CDCl$_3$, TMS=0 ppm) δ: 0.04 (3H, s), 0.06 (3H, s), 0.85-0.89 (12H, m), 1.23 (6H, d, J=6.3 Hz), 1.22-1.82 (27H, m), 2.04-2.08 (1H, m), 2.25-2.28 (4H, m), 3.92 (4H, m), 4.38-4.39 (1H, m), 5.01 (1H, septet, J=6.2 Hz)

Example 5

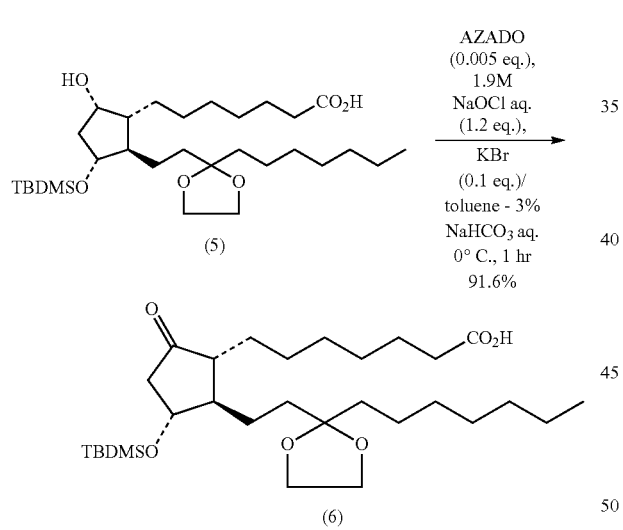

An alcohol compound (5) 0.200 g (0.37 mmol) was dissolved in toluene 1.4 ml, and then AZADO (1 mg/ml in toluene 0.3 ml, 0.0018 mmol) was added thereto. The mixture was cooled in an ice bath to 0° C. Three percent aqueous sodium hydrogen carbonate 2.19 ml (0.74 mmol) and potassium bromide 4.4 mg (0.037 mmol) were added thereto. Then, about 1.9M aqueous sodium hypochlorite 0.23 ml (0.44 mmol) was added dropwise to the reaction, and the mixture was stirred at 0° C. for 1 hour. The reaction mixture was then added with saturated aqueous sodium thiosulfate and dilute hydrochloric acid, and the mixture was extracted three times with ethyl acetate. The extract was washed with water, followed by saturated saline, and then dried with anhydrous magnesium sulfate, filtered and concentrated under reduced pressure. The residue was purified with silica gel flash chromatography (column: FL60D with a water content of 15%; 60 g, ethyl acetate:hexane=1:2) to give compound (6) as colorless oil. Yield 0.1825 g (91.6%)

$^1$H-NMR (400 MHz in CDCl$_3$, TMS=0 ppm) δ: 0.05 (3H, s), 0.08 (3H, J=6.1, 18.1 Hz), 2.33 (2H, t, J=7.6 Hz), 2.54-2.60 (1H, m), 3.92-3.96 (4H, m), 4.01-4.06 (1H, m)

What is claimed is:

1. A method for manufacturing a fatty acid derivative represented by formula (I):

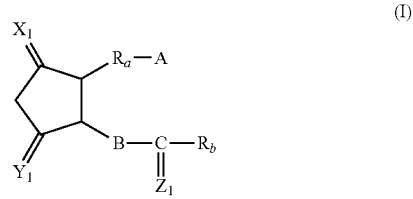

wherein $X_1$ is

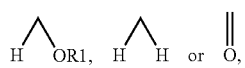

wherein R1 is a protecting group for hydroxy group;
$Y_1$ is

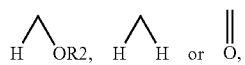

wherein R2 is a protecting group for hydroxy group;
$Z_1$ is

wherein R3 and R4 are hydrogen atom, halogen atom, lower alkyl or lower alkoxy; when R3 or R4 is lower alkoxy, then the other of R3 and R4 is lower alkoxy; and when R3 and R4 are lower alkoxy, R3 and R4 may be linked together to form a ring structure;
provided that at least one of $X_1$ and $Y_1$ is

A is —CH$_3$, —CH$_2$OH, —COCH$_2$OH, —COOH or a salt, ether, ester or amide thereof;
B is a single bond, —CH$_2$—, —CH$_2$—CH$_2$—, —CH=CH— or —C≡C—, —CH$_2$—CH$_2$—CH$_2$—, —CH=CH—CH$_2$—, —CH$_2$—CH=CH—, —C≡C—CH$_2$— or —CH$_2$—C≡C—;
Ra is bivalent saturated or unsaturated lower-medium aliphatic hydrocarbon group, which is unsubstituted or substituted by halogen atom, lower alkyl, lower alkoxy, oxo, aryl or heterocyclic group, provided that one or more carbon atoms of the aliphatic hydrocarbon group may optionally be replaced with oxygen, nitrogen or sulfur atom; and Rb is hydrogen atom; saturated or unsaturated lower-medium aliphatic hydrocarbon group which is unsubstituted or substituted by a halogen, oxo, hydroxy, lower alkoxy, lower alkanoyloxy, cyclo(lower)alkyl, cyclo(lower)alkyloxy, aryl, aryloxy, heterocyclic or heterocyclic oxy; cyclo(lower)alkyl; cyclo(lower)alkyloxy; aryl; aryloxy; heterocyclic; or heterocyclic oxy, which comprises the step of, reacting a compound of formula (II):

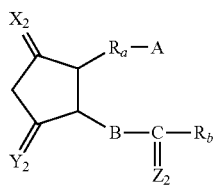
(II)

wherein, $X_2$ is the same as $X_1$ except for when $X_1$ is

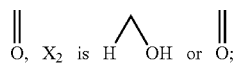
O, $X_2$ is H OH or O;

$Y_2$ is the same as $Y_1$ except for when $Y_1$ is

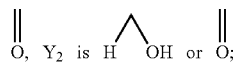
O, $Y_2$ is H OH or O;

$Z_2$ is the same as $Z_1$;

provided that at least one of $X_2$ and $Y_2$ is

H OH;

and,

A, B, Ra and Rb are the same as above;

with a co-oxidizer under the presence of an azaadamantane-N-oxyl compound.

2. The method of claim 1, wherein A is —COOH or a salt, ester or amide thereof.

3. The method of claim 1, wherein the azaadamantane-N-oxyl compound is 2-azaadamantane-N-oxyl.

4. The method of claim 1, wherein the azaadamantane-N-oxyl compound is 1-methyl-2-azaadamantane-N-oxyl.

5. The method of claim 1, wherein the azaadamantane-N-oxyl compound is 2-hydroxy-2-azaadamantane.

6. The method of claim 1, wherein the azaadamantane-N-oxyl compound is 2-hydroxy-1-methyl-2-azaadamantane.

* * * * *